United States Patent
Schlotterbeck Suárez et al.

(10) Patent No.: US 10,987,392 B2
(45) Date of Patent: Apr. 27, 2021

(54) **METHOD FOR PREVENTING AND CONTROLLING VIRAL INFECTIONS IN SALMONID FISH USING *QUILLAJA SAPONARIA* EXTRACTS**

(71) Applicant: SAPONIN RESEARCH CENTER S.A., Santiago de Chile (CL)

(72) Inventors: Trinidad Schlotterbeck Suárez, Santiago de Chile (CL); Hernán Alberto Cañon Jones, Santiago de Chile (CL); Mario Hernán Castillo Ruiz, Santiago de Chile (CL); Hernán Danilo Cortés González, Vña del Mar (CL); Ricardo Manuel San Martín Gamboa, Santiago de Chile (CL)

(73) Assignee: SAPONIN RESEARCH CENTER S.A., Santiago de Chile (CL)

( * ) Notice: Subject to any disclaimer, the term of this patent is extended or adjusted under 35 U.S.C. 154(b) by 23 days.

(21) Appl. No.: 16/527,646

(22) Filed: Jul. 31, 2019

(65) Prior Publication Data

US 2019/0350994 A1    Nov. 21, 2019

Related U.S. Application Data

(62) Division of application No. 15/543,978, filed as application No. PCT/CL2016/050045 on Jul. 29, 2016.

(51) Int. Cl.
*A61K 36/185* (2006.01)
*A61K 36/73* (2006.01)
(Continued)

(52) U.S. Cl.
CPC ............ *A61K 36/185* (2013.01); *A23K 10/30* (2016.05); *A23K 50/80* (2016.05); *A61K 9/0053* (2013.01);
(Continued)

(58) Field of Classification Search
CPC .................................................. A61K 36/185
See application file for complete search history.

(56) References Cited

U.S. PATENT DOCUMENTS

| | | | |
|---|---|---|---|
| 2005/0074508 A1 | 4/2005 | San Martin | |
| 2007/0196517 A1 | 8/2007 | San Martin | |
| 2008/0226682 A1 | 9/2008 | Brake et al. | |

FOREIGN PATENT DOCUMENTS

| | | |
|---|---|---|
| CL | 200402942 | 3/2006 |
| WO | 0151083 A2 | 7/2001 |

(Continued)

OTHER PUBLICATIONS

Tobar, Ivan, et al. "Successive Oral Immunizations against Piscirickettsia salmonis and Infectious Salmon Anemia Virus are Required to Maintain a Long-Term Protection in Farmed Salmonids", May 27, 2015. Frontiers in Immunology, (6) 244) (7 pages).

(Continued)

*Primary Examiner* — Rosanne Kosson
(74) *Attorney, Agent, or Firm* — Procopio, Cory, Hargreaves & Savitch LLP

(57) ABSTRACT

The present invention provides a new method for preventing and controlling viral diseases in salmonid fish using *Quillaja* extracts, wherein said method comprises administering to salmonid fish an effective amount of a medicinal composition comprising a *Quillaja saponaria* extract as active ingredient.

3 Claims, 1 Drawing Sheet

(51) Int. Cl.
    A23K 50/80      (2016.01)
    A23K 10/30      (2016.01)
    A61P 31/14      (2006.01)
    A61K 9/00       (2006.01)
(52) U.S. Cl.
    CPC ............ *A61K 9/0056* (2013.01); *A61K 36/73* (2013.01); *A61P 31/14* (2018.01)

(56) References Cited

FOREIGN PATENT DOCUMENTS

| | | |
|---|---|---|
| WO | 2014052378 A2 | 4/2014 |
| WO | 2015155293 A1 | 10/2015 |
| WO | 2015179840 A1 | 11/2015 |

OTHER PUBLICATIONS

Tapia, D., et al. "Detection and Phylogenetic Analysis of Infectious Pancreatic Necrosis Virus in Chile" Oct. 27, 2015. Diseases of Aquatic Organisms, 116 (3), 173-184, (12 pages).

Semapesca (2013). Informe sanitario de salmonicultura en centros marinos 2012, Servicio Nacional de Pesca y Acuicultura. Valparaiso Government of Chile. (30 pages). Untranslated.

Jensen, Britt Bang., et al. "Risk Factors for Outbreaks of Infectious Pancreatic Necrosis (IPN) and Associated Mortality in Norweigian Salmonid Farming", Diseases of Aquatic Organisms, 114 (3), 177-187 (2015). (11 pages).

Bragg, R.R., and Combrink, M.E, "Isolation and Identification of Infectious Pancreatic Necrosis (IPN) Virus From Rainbow Trout in South Africa", Doctoral Dissertation (2015) Bull. Eur. Ass. Fish Pathol. 7 95), 118, 1987 (3 pgs).

Vike, Siri, et al. "Release and Survival of Infectious Salmon Anaemia (ISA) Virus During Decomposition of Atlantic Salmon (*Salmo salar* L.)" (2014). Aquaculture, 420, 119-125 (7 pages).

Robledo, Diego, et al. "Gene Expression Comparison of Resistant and Susceptible Atlantic Salmon Fry Challenged with Infectious Pancreatic Necrosis Virus Reveals a Marked Contrast in Immune Response" (2016). BMC Genomics, 17 (1), 1). (16 pages).

Kousoulaki, Katerina, et al. "Metabolism, Health and Fillet Nutritional Quality in Atlantic Salmon (*Salmo salar*) Fed Diets Containing n-3-rich Microalgae" (2015). Journal of Nutritional Science, vol. 4, e24, pp. 1-13 (13 pages).

San Martin, Ricardo and Briones, Reinaldo "Industrial Uses and Sustainable Supply of Quillaja Saponaria (Rosaceae) Saponins" (1999). Economic Botany, 53 (3), 302-311) (10 pages).

San Martin, Ricardo and Briones, Reinaldo "Quality Control of Commercial Quillaja (Quillaja Saponaria Molina) Extracts by Reverse Phase HPLC" (2000). Journal of the Science of Food and Agriculture, 80 (14), 2063-2068). (6 pages).

Maier, Christiane, et al. "Phenolic Constituents in Commercial Aqueous Quillaja (Quillaja saponaria Molina) Wood Extracts" Jan. 27, 2015. Journal of Agricultural and Food Chemistry, 63 (6), 1756-1762 (7 pages).

Elizondo, Ernesto A. Moya, et al. "Evaluation of a Quillaja Saponaria Saponin Extract for Control of Powdery Mildew of Wheat and Squash" (2010). Agro south, vol. 38 (2), 87-96 (10 pages).

Wang, Yujuan, et al., "Adjuvant Effect of Quillaja saponaria Saponin (QSS) on Protective Efficacy and IgM Generation in Turbot (*Scophthalmus maximus*) upon Immersion Vaccination" International Journal of Molecular Sciences, 2016, 17, 325; (13 pages).

Fernandes, Rosangela Do Nascimento, (2014) Use of Quillaia saponin (Quillaja saponaria Molina) in Juveniles of Pacu, Universidade Estadual Paulista, Faculty of Agricultural Sciences and Veterinary Center Aqüicultura, Brazil PhD Thesis Jaboticabal, 2014 (115 pages). Untranslated.

Vinay, Tharabenahalli-Nagaraju, et al. "Toxicity and Dose Determination of Quillaja Saponin, Aluminum Hydroxide and Squalene in Olive Flounder (*Paralichthys olivaceus*)" (2014), Veterinary immunology and immunopathology, 158 (1), 73-85 (14 pages).

Krogdahl, Ashild, et al. "Soya Saponins Induce Enteritis in Atlantic Salmon (*Salmo salar* L.)" Mar. 23, 2015, Journal of Agricultural and Food Chemistry 2015, 63, 3887-3902 (16 pages). Copyright 2015 American Chemical Society DOI: 10.1021/jf506242t.

Francis, George, et al., "Effects of Long Term Feeding of Quillaja saponins on sex ratio, muscle and serum cholesterol and LH levels in Nile tilapia (*Oreochromis niloticus* (L))." Comparative Biochemistry and Physiology Part A: Toxicology & Pharmacology 133.4 (2002): 593-603. (11 pages).

Diagnostic Manual for Aquatic Animal Diseases, 3rd edn. OIE, Paris 2000 (281 pages).

METHOD FOR PREVENTING AND CONTROLLING VIRAL INFECTIONS IN SALMONID FISH USING *QUILLAJA SAPONARIA* EXTRACTS

TECHNICAL FIELD

The present invention relates to the aquaculture industry, and particularly provides a new method for preventing and controlling viral diseases in salmonid fish using extracts of *Quillaja saponaria* trees.

BACKGROUND OF THE INVENTION

Salmon farming industry has grown significantly worldwide in the last two decades; particularly in Chile this economic sector has become one of the most important for the country. However, different viral diseases infect fish and have a negative effect on production.

Among the viral diseases affecting fish, infectious pancreatic necrosis (IPN) is a highly contagious disease affecting farmed salmonids which causes high mortality rates in fry during their first feeding stage and in juveniles (smolts) after transfer to seawater. This disease is one of the most important diseases in Chile and is considered endemic in the country, causing great economic losses in the salmon industry (Tapia, losses D. et al. (2015). Diseases of Aquatic Organisms, 116 (3), 173-184). Its etiologic agent is the IPN virus (IPNv). Currently, the IPNv is one of the pathogens most frequently detected by diagnostic laboratories in marine and freshwater farms, and is the second leading cause of mortality in adult Atlantic salmon in fish farms in Chile (Sernapesca (2013). Informe sanitario de salmonicultura en centros marinos, 2012, Servicio Nacional de Pesca y Acuicultura. Valparaiso). However, the geographical distribution of this pathogen is not limited to Chile and it has been historically found in Norway (Diseases of Aquatic Organisms, 114 (3), 177-187 Jensen, B. et al. (2015)) and more recently in steelhead trout in South Africa (doctoral Dissertation Bragg, R R (2015). Isolation and Identification of Infectious Pancreatic Necrosis Virus from Rainbow trout (*Salmo gairdneri* Richardson) in South Africa), reaching a worldwide distribution. Given the negative impact on the health of fish caused by this virus, there is a constant need to seek alternatives for its control.

The virus that causes infectious pancreatic necrosis belongs to the Birnaviridae family and *Aquabirnavirus* genus, and it is characterized by having a non-enveloped capsid with a genome consisting of double stranded RNA. Clinical symptoms of infection include swelling of the abdomen and eyes, skin darkening, necrosis of the pancreatic tissue and spiral swim; which can cause death of fish. In the juvenile stage of freshwater, an outbreak of IPNv can cause 100% mortality. To prevent this viral agent various vaccination strategies have been provided, however, IPNv outbreak control depends on the biosafety of the farms and the level of resistance of fish (Robledo, D. et al. (2016). BMC Genomics, 17 (1), 1).

Another viral agent in the aquaculture industry is the infectious salmon anemia virus (ISA) which attacks mainly salmonids and can lead to high mortality rates in the population of affected fish, threatening the main areas of fish farming in the North Atlantic Ocean and in Chile. The ISA virus (ISAv) belongs to the Orthomyxoviridae family, *Isavirus* genus and has a single-stranded RNA genome with envelope (Vike, S. et al. (2014). Aquaculture, 420, 119-125). The virus inside the fish infects all organs but preferably the endothelium, causing bleeding, lethargy, abdominal distension and severe anemia in the affected fish. The mortality caused by this disease is high and few fish remain alive as carriers. In Chile, the first outbreaks occurred in mid-2007 and the solution was the elimination of all salmon infected.

To destroy cells infected with intracellular pathogens is critical that the vaccine or other non-antibiotic alternatives induce the cellular immune response. Currently, due to the nature of the virus, control using medicinal compounds is not effective or economically viable and prevention measures consist of maintaining a strong biosafety (imported egg control), use of vaccines and total elimination of sea-cages infected.

Multiple strategies to increase the resistance of fish to pathogens have been used in parallel with the development of vaccines. As an alternative, the administration of food for fish that improves health has been used. In this regard, diets rich with microalgae containing polyunsaturated fatty acids, glycans, carotenoids, among others have been used. These ingredients can promote fish welfare, improve intestinal health and increase resistance to disease (Kousoulaki, K. et al. (2015). Journal of Nutritional Science, 4, e24). Nevertheless, said compounds that do not induce a cellular mediated immune response (CIR), have a low efficacy in the control of viral diseases.

Therefore, there is a need for the development of non-antibiotic alternatives that induce both Cellular Mediated Immunity (CMI), and a Humoral Mediated Immunity (HMI) that can attack intracellular pathogens and eliminate infected cells (Munang'andu HM, Evensen Ø. (2019). Fish Shellfish Immunol 85, 132-140).

*Quillaja saponaria* Molina (common name Quillay) is a native tree of Chile primarily used as a soap substitute due to the presence of saponins (San Martin, R. (1999). Economic Botany, 53 (3), 302-311). Saponins can be obtained industrially as powder or liquid extracts, and may be in a purified state, partially purified or unpurified. These extracts are marketed by several companies, being one of the most important Natural Response and Desert King (San Martin, R. and Briones, R. (2000). Journal of the Science of Food and Agriculture, 80 (14), 2063-2068).

To date, the extracts rich in saponins are used as natural emulsifiers in cosmetics, food and beverages. Additionally, these are used as adjuvants for vaccine production and pharmaceutical formulations (Maier, C. et al. (2015). Journal of Agricultural and Food Chemistry, 63 (6), 1756-1762). Other uses have also been as a biocide to eliminate nematodes (US 2005/0074508 A1), mollusks (US 2007/0196517 A1) and fungi (Moya Elizondo, E. A. et al. (2010). Agro Sur, 38 (2), 87-96).

In the review of Wang, Y. et al. (2016), International Journal of Molecular Sciences, 17 (3), 325, describes the use of saponins in aquatic animals showing that these can modulate the immune system of shrimp and fish, and also promote the growth of the latter. However, the document states that most saponins are unstable in aqueous conditions and are very toxic to fish at high concentrations.

Prior art analysis regarding the application of *Quillaja* extracts in fish, showed patent application WO 2015/155293 A1 disclosing an oral food additive for use in the prevention and/or treatment of infections and particularly describes a composition comprising *Quillaja saponaria* saponins for prophylactic treatment of the ectoparasite copepod *Caligus* in fish. The experimental evidence provided by this document does not sustain the beneficial effect against other pathogens such as bacteria and virus that affect salmonid fish.

Zo Patent application WO 2015/179840 A1 describes combinations or compositions comprising *Yucca schidigera* and *Quillaja saponaria*, and further include antimicrobials, antibiotics and anticoccidial agents, for administration to animals to prevent diseases. As a general disclosure, it describes that can be applied to fish orally.

Patent WO 01/51083 A2 application discloses the adjuvant composition comprising a saponin and an oligonucleotide comprising at least one CpG unmethylated dinucleotide. Preferably, the composition includes saponins derived from *Quillaja saponaria*, and most preferably, the saponin is chemically modified or includes a substantially pure saponin (QS7, QS17, QS18 or QS21). No description is done for the use in fishes.

Chilean patent application CL 2942-2004 discloses a food additive fish formulated with purified extract of *Quillaja saponaria* Molina comprising 15-25% w/w of triterpene saponins obtained from the extract and 75-85% w/w of potato maltodextrin. This document discloses that the food additive improves the fish growth and feed conversion but does not mention that this food additive could be effective against pathogens such as virus and bacteria that affect salmonid fish.

The PhD thesis of Fernandes, R. N, (2014) Using *Quillaia* saponin (*Quillaja saponaria* Molina) em juvenis of pacu, Universidade Estadual Paulista, Faculty of Agricultural Sciences and Veterinary Center Aqüicultura, Brazil, describes a study wherein the effect of administering *Quillaja* saponins in doses from 100 to 400 mg/kg in pacu fish (*Piaractus mesopotamicus*). Following 15 days of feeding fish with *Quillaja* saponins, 325 fish were inoculated with *Aeromonas hydrophila* and clinical signs were observed. After seven days, the survival of pacu fish against experimental infection was higher in fish fed with *Quillaja* saponins in a dose of 200 mg/kg.

On the other hand, Vinay et al. (2014), *Veterinary immunology and immunopathology*, 158 (1), 73-85, describes an evaluation of the systemic effect of *Quillaja* saponins administered intraperitoneally as vaccine adjuvant in *Paralichthys olivaceus*. This study showed that saponins are good inducers of inflammation, but are also toxic to the fish. Saponins concentrations of 500, 160, 50, 16 and 5 µg/fish produced 95%, 65%, 20%, and 5% mortality rates, respectively, with a lethal dose ($LD_{50}$) of 22.4 mg/kg. The results determined that the toxic effect of saponins depended on the level of purification and the source of the product. Finally, the authors found that a concentration of 3.4 mg/kg of fish is toxic when is administered intraperitoneally, and it is recommended to use a lower concentration in *Paralichthys olivaceus*.

Regarding disclosures of saponins from sources other than *Quillaja saponaria*, Krogdahl et al. (2015), *Journal of Agricultural and Food Chemistry*, 63 (15), 3887-3902 discloses that soybean saponins administered orally as feed additive in doses of 2-10 g/kg produced intestinal inflammation in Atlantic salmon (*Salmo salar*), and the severity is dose-dependent.

This analysis of prior art shows that, although *Quillaja saponaria* saponins have been described for various uses and applications, they are used mainly as adjuvants and they are not associated with treatment of viral infections in commercial fish.

SUMMARY OF THE INVENTION

The present invention discloses a new method for controlling and preventing viral diseases in salmonid fish using *Quillaja* extracts, wherein said method comprises administering to salmonid fish an effective amount of a medicinal composition comprising a *Quillaja saponaria* extract as active ingredient and an appropriate excipient; wherein said *Quillaja saponaria* extract contains saponins.

Such medicinal preparation for salmonid fish is administered orally in a preferably dose range of 0.9 to 12 mg of saponins/kg of live weight of fish per day. In a preferred embodiment, administration to fish is performed orally in combination with food.

In a preferred embodiment, the viral diseases are caused by a virus belonging to the families of the group comprising Birnaviridae, and Orthomyxoviridae, genus *Aquabirnaviridae* and *Isavirus*, respectively; and in particular for the viruses of the pancreatic necrosis and infectious salmon anemia, respectively.

The present invention is intended for salmonid fish, preferably salmonid fish selected from the group consisting of *Salmo salar, Salmo trutta, Salmo gairdnerii, Oncorhynchus mykiss* or *Oncorhynchus kisutch* species.

DETAILED DESCRIPTION OF THE INVENTION

Figures 1, 2:
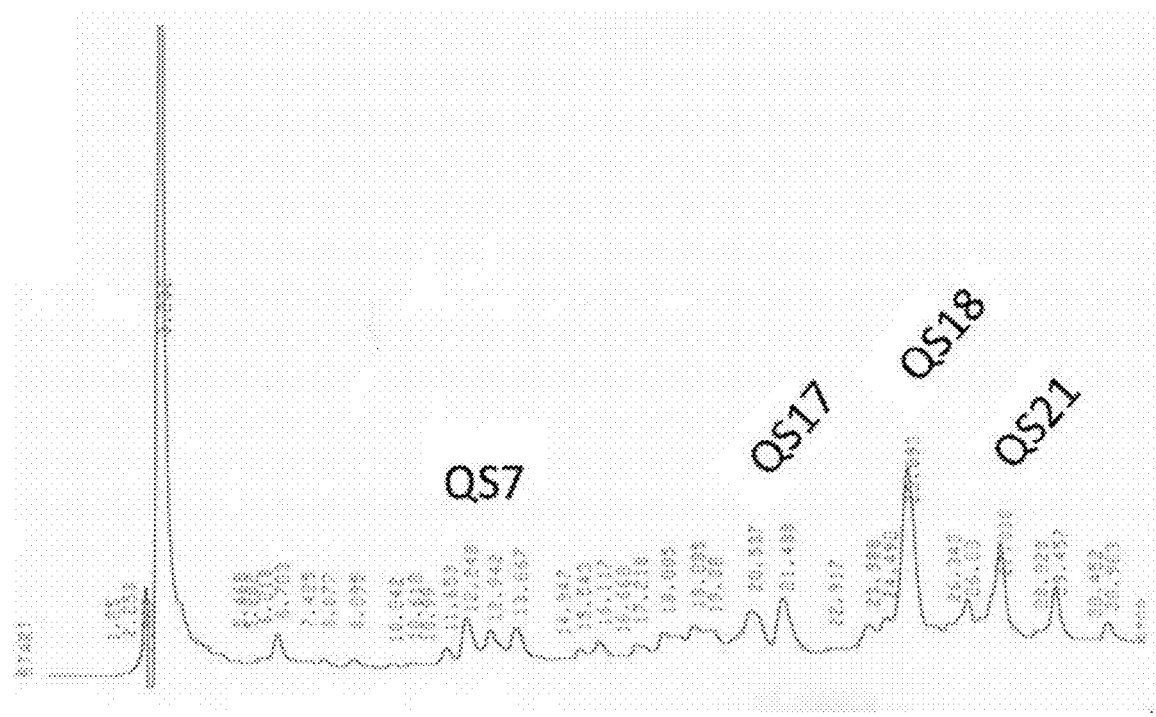
FIG. 1 is the chromatographic profile of a complete *Quillaja saponaria* Molina extract measured by HPLC, where the main saponins QS7, QS17, QS18 and QS21 are indicated.
FIG. 2 is an image obtained by optical microscopy of ASK salmonid cell line in the presence of different concentrations of *Quillaja* extracts UD100-Q (Ultra Dry® 100-Q) and QD100 (*Quillaja* Dry® 100).

The present invention describes a method for preventing and controlling viral infections that affect salmonid fish using plant extracts of *Quillaja saponaria*. Surprisingly, the inventors have found that different extracts of *Quillaja saponaria*, a Chilean endemic tree, particularly *Quillaja saponaria* Molina saponins, used as the only active ingredient in a medicinal composition have a protective effect against viral infections affecting salmonid farming, probably because said extracts induce a cellular mediated immune response needed to control intracellular pathogens infections in aquaculture systems.

The inventors have tested and acquired appropriate dose concentrations of *Quillaja* extracts to be used safely in salmon, without altering pathophysiological treated individuals.

All technical and scientific terms used to describe the present invention have the same meaning understood by a person having a basic knowledge in this technical field. Notwithstanding, to define the scope of the invention more clearly, a list of terminology used in this description is included down below.

It should be understood that as used herein, the term "prevention" or "preventing" an infection refers to practical solutions designed to prevent the damages caused by infections (CDC's Infectious Disease. https://www.cdc.gov/ddid/framework.html). The prevention of disease in human and animals includes the implementation of the necessary practices to prevent the occurrence of a disease, but it does not imply that the disease does not occur. In fact, the actions that are taken to prevent a disease, including the use of vaccines, are aimed at increasing the "resistance" of patients (animals/humans) to this disease, i.e. the ability of the individual to moderate the cycle of life of the pathogen (its infectious cycle), which allows to reduce the transmission of the infection and therefore the severity of the disease at population level.

It should be understood that as used herein, the term "control" or "controlling" an infection refers to practical solutions that are applied to reduce the transmission of infections from one individual to another (Population Health Division, San Francisco Department of Public Health, Disease Prevention & Control. https://www.sfcdcp.org/communicable-disease/infection-control-practices/).

It should be understood that as used herein, the term "salmonid fish" refers to fish that belong to the Salmonidae family, which includes salmon, trout, chars, among others.

It should be understood that as used herein, the term "effective amount" refers to an amount of a compound, composition and/or formulation of the invention that is sufficient to produce a desired effect and is not toxic.

The present invention relates to a method for preventing and controlling viral infections in salmonid fish using effective amounts of a medicinal composition that comprises *Quillaja saponaria* extracts as the only active ingredient and an appropriate excipient; wherein said *Quillaja Saponaria* extract contains saponins.

The *Quillaja saponaria* extracts have a specific profile of saponins. In all cases, the profiles of these extracts are saponins own exclusive of *Quillaja saponaria*, as seen in the chromatographic profile of FIG. 1, either in purified extracts, partially purified or unpurified.

Entire or unfractionated extracts of preferably *Quillaja saponaria* Molina have a distinctive profile and own saponins containing over 100 types of chemically different saponins. *Quillaja* saponins are high molecular weight glycosides, containing a hydrophobic triterpenic nucleus and two hydrophilic sugar chains. The main saponins from this plant are QS7, QS17, QS18 and QS21 (Kensil C. R. (1991). J Immunol 146: 431-437), as seen in the chromatographic profile of FIG. 1.

The relative concentrations of these saponins depend on the source of the raw material that comes from the *Quillaja saponaria* tree, and also varies between the different species of trees. Additionally, the partially purified extracts (from 2 to 90% w/w or w/v of saponins depending on powder or liquid product) contain non-saponin compounds, which mainly include a mixture of polyphenols and, in smaller amounts, other sugars. Extracts of *Quillaja* saponins can be obtained industrially as powder or liquid extracts, with varying degrees of purification. For example, for the purposes of the present invention, various commercial extracts of *Quillaja saponaria* may be used, such as those shown in Table 1 below.

TABLE 1

Commercial extracts (Desert King Chile) of *Quillaja saponaria* useful for the present invention.

| Product name | Description |
| --- | --- |
| Ultra Dry ® 100-Q | *Quillaja saponaria* Molina powder extract, mainly containing triterpenoid saponins up to 65% w/w. |
| Quillaja Dry ® 100 | *Quillaja saponaria* Molina powder extract, mainly containing triterpenoid saponins up to 25% w/w. |
| Vax Sap ® | Highly purified *Quillaja saponaria* Molina powder, mainly containing triterpenoid saponins >90% w/w. |
| QL 1000 ® | Liquid extract mainly of *Quillaja saponaria* Molina at a concentration of 8% w/v of triterpenoid saponins. |

TABLE 1-continued

Commercial extracts (Desert King Chile) of *Quillaja saponaria* useful for the present invention.

| Product name | Description |
| --- | --- |
| QL Perm ® | Liquid extract mainly of *Quillaja saponaria* Molina at a concentration of 2% w/v of triterpenoid saponins. |

The medicinal composition also includes appropriate excipients that may be any additive necessary for preparing said medicinal composition such as lactose, corn starch, silicon dioxide, binding agents, emulsions, surfactants, fatty acids, fats, oils, among others well known by experts of this area.

In a preferred embodiment of the present invention, the medicinal composition is administered to salmonid fish orally, in a liquid or solid form, but alternative methods of administration may be used such as immersion (bath treatments) or injections. Preferably, the medicinal composition is administered to the fish in combination with fish food. Said medicinal composition may be incorporated into the fish food during its production, for example, prior to pelleting, or may be incorporated into the fish food pellets, or granules impregnating them with the medicinal composition. Preferably, the *Quillaja saponaria* extracts are mixed with fish food in a pellet form, which is mixed with an equivalent to 2% of oil/weight of the pellet to impregnate, to adhere the extract to the food. Examples of fish diets widely known in the industry are produced by Ewos®, BioMar®, Salmofood®, Skretting®, among others. In a preferred embodiment, the food composition comprises food additives appropriate for oral administration in salmonids, such as fishmeal, fish and/or vegetable oil, vitamins, minerals, among others well known by experts of the area.

In a preferred embodiment, the medicinal composition is administered orally in a dose ranging from 0.9 to 12 mg saponins/kg of live weight of fish per day, but it may vary depending on the species of the salmonid fish treated. The medicinal composition could be administered to the salmonid fish in a single dose per day or could be equally divided in several doses per day, as long as the total dose required per day is administered. The medicinal composition could be administered through the entire productive cycle of fish from fry to adults, or could be administered in a specific time window, for example, only during months with higher probabilities of viral infection outbreak. Taking into account that virus outbreaks do not have a certain seasonality, the product can be supplied during the whole fish breeding and fattening cycle, or in time windows that the producer sees of greater risks of viral infections in his production area. This is because IPN outbreaks, generally associated with management activities that generate stress on animals, are a problem during the freshwater breeding stage, and during the first months of transferring fish to the sea, while presentations of ISA virus, can happen at any time of the year.

The present invention encompasses the use of *Quillaja* extracts against virus that affect salmonid fish. Surprisingly, the administration of *Quillaja saponaria* extracts to salmonid fish is equally effective for preventing and controlling both non-enveloped virus such as IPNv and enveloped virus such as the infectious salmon anemia virus (ISAv), probably due to its capacity to induce both Cellular Mediated Immunity (CMI), and a Humoral Mediated Immunity (HMI). CMI induced by *Quillaja saponaria* saponins eliminate infected cells, and HMI induced by *Quillaja saponaria* saponins induce the antibodies production that neutralize pathogens out of the cells.

The administration of *Quillaja saponaria* extracts to salmonid fish is effective preventing and controlling virus belonging to the Birnaviridae family, such as the Infectious pancreatic necrosis virus (IPNv), and Orthomyxoviridae family, such as the infectious salmon anemia virus (ISAv), or any other virus that affect the health of salmonid fish, either in freshwater or seawater.

The most susceptible species of salmonid fish are rainbow trout (*Oncorhynchus mykiss*), brook trout (*Salvelinus fontinalis*), brown trout (*Salmo trutta*), Arctic char (*Salvelinus alpinus*), Atlantic salmon (*Salmo salar*), Pacific salmon (*Oncorhynchus* spp.), chum salmon (*Oncorhynchus keta*), chinook salmon (*Oncorhynchus tshawytscha*), among others.

In particular, infectious pancreatic necrosis (IPN) is a highly contagious viral disease affecting fish of all species of salmon. The most susceptible species are rainbow trout (*Oncorhynchus mykiss*), brook trout (*Salvelinus fontinalis*), brown trout (*Salmo trutta*), Atlantic salmon (*Salmo salar*), and Pacific salmon (*Oncorhynchus* spp.). The stages most affected by this viral disease are fingerlings, but also the disease occurs in young or Atlantic salmon smolts within the first weeks after transfer from fresh water to seawater. The classic signs of outbreaks of IPN are a sudden increase, and usually progressive, daily mortality, accompanied by clinical signs such as increased dark pigmentation, distended abdomen and corkscrew swimming motion. IPNv also causes disease in other species of food fish such as yellowtail (*Seriola quinqueradiata*), turbot (*Scophthalmus maximus*), halibut (*Hippoglossus hippoglossus*) and Atlantic cod (*Gadus morhua*), which also can be treated with *Quillaja saponaria* extracts for medicinal purposes, and in general on any fish species susceptible to infection of IPNv.

The most important virus that affects fish is the infectious salmon anemia virus (ISAv). Fish infected with this virus show clinical signs that may include lethargy, anemia, leucopenia, ascites, exophthalmos, skin darkening and high mortality. Severe anemia is usually associated with very pale gills. ISAv outbreaks occur primarily in Atlantic salmon (*Salmo salar*) but infections have been reported in other species such as Coho salmon (*Oncorhynchus kisutch*) and experimentally in rainbow trout (*O. mykiss*). Natural reservoirs of the virus are river trout (*Salmo trutta*), chum salmon (*O. keta*), chinook salmon (*O. tshawytscha*) and Arctic char (*Salvelinus alpinus*). Also, the virus affects other non-salmonid species, such as herring (*Clupea harengus*), Atlantic cod (*Gadus morhua*) and pollack (*Pollachius virens*), where *Quillaja saponaria* extracts can also be used for medicinal purposes and generally any kind of susceptible fish to infections by the virus.

Examples of implementation of the invention have been included for the purpose of illustrating the invention, with the preferred embodiments and comparative examples, but in no case to be considered as a restriction to the scope of the patent application, which it is only delimited by the content of the claims appended hereto.

EXAMPLES

Example 1: Evaluation of In Vitro and In Vivo Toxicity of *Quillaja* Extracts In Vitro Citotoxicity Assay in Salmon Cell Lines.

Assays with *Quillaja* extracts products were tested on cell monolayers derived from salmon in order to assess the citotoxicity. The cell lines used were SHK-1 and ASK. SHK-1 line, described as macrophage-like cells (*Salmo salar*, ECACC 97111106 Number, European Collection of Cell Culture, Salisbury, Wilts, SP4 0JG, UK) was cultured at 15° C. in Leibovitz 15 medium (L-15, Gibco, Invitrogen, Carlsbad, Calif., USA) supplemented with 10% v/v fetal bovine serum (Hyclone, Thermo Fisher Scientific, Logan, Utah, USA), 4 mM L-glutamine (Gibco), 1% v/v 2-mercaptoethanol (2-ME, Gibco) and 50 µg/mL gentamicin (US Biological, Swampscott, Mass., USA). The cell line ASK (Atlantic Salmon Kidney, ATCC® CRL2747™) was cultured at 16° C. in Leibovitz (L-15, Hyclone, Thermo Scientific), supplemented with gentamicin (50 µg/mL), L-glutamine (4 mM) (Gibco, Thermo Scientific), 2-mercaptoethanol 1% (v/v) (2-ME, Gibco) and 10% fetal bovine serum (v/v) (FBS, Hyclone).

All *Quillaja* extracts products (Table 2) were prepared in MEM or 15 Leibovitz medium at a concentration of 1 mg/mL, being dissolved at 37° C. for 3 hours with gentle stirring. All prepared solutions of these extracts were filtered through a 0.22 µm nitrocellulose membrane of to avoid contamination in cell cultures. The evaluated dilutions were prepared by serial dilutions from the standard solution.

To assess the cytotoxicity of *Quillaja* extracts in salmonid cell lines, $5 \times 10^5$ cells/well were seeded in 6-well plates and incubated in 2 mL of culture medium as final volume for 72 hours at 15° C. After this time the culture medium was replaced with fresh medium and the confluency was verified. After 24 hours, cells were incubated with the different *Quillaja* extracts in 1 mL of culture medium. Cytotoxicity assessment was made after 24 hours incubation with *Quillaja* extracts. For this, the cells were washed twice with cold PBS and then disaggregated using a solution with 0.05% trypsin and 0.02% EDTA. Cells were analyzed by flow cytometry (FACS Canto II (Becton Dickinson) and incorporation of propidium iodide was determined as a marker for dead cells. Cells were incubated with a solution of ethanol as a positive control of cell death. As negative control, cells were incubated without *Quillaja* extracts, but were subjected to the same conditions. Additionally, cytotoxicity was assessed by visualizing cells by light microscopy.

Results indicated that the concentration that exhibited a 50% of cell death ($CC_{50}$) was between 3.5 and 83.4 µg/mL and the $CC_{50}$ varied between 4.7 and 92.6 µg/mL, depending on the product used as indicated in Table 2. FIG. 2 shows representative results with products QD 100 (*Quillaja Dry®* 100) and UD 100Q (Ultra Dry® 100-Q) by observing the cell monolayer through optical microscopy.

TABLE 2

Cell citotoxicity ($CC_{50}$) by flow citometry using propidium iodide.

| Product | $CC_{50}$ in SHK-1 (µg/mL) | $CC_{90}$ in SHK-1 (µg/mL) |
|---|---|---|
| Vax Sap ® | 20.4 | 25.3 |
| Ultra Dry ® 100-Q | 22.1 | 29.2 |
| Quillaja Dry ® 100 | 83.4 | 92.6 |

TABLE 2-continued

Cell citotoxicity ($CC_{50}$) by flow citometry using propidium iodide.

| Product | $CC_{50}$ in SHK-1 (µg/mL) | $CC_{90}$ in SHK-1 (µg/mL) |
|---|---|---|
| QL 1000 ® | 3.7 | 6.5 |
| QL Perm ® | 3.5 | 4.7 |

In Vivo Citotoxicity Assay in Fish.

To determine the short term oral toxicity (60 days), 550 Atlantic salmon (Salmo salar) clinically healthy fishes were taken, with an average weight of 9.5 g. Prior to the experiment the fish were acclimated for 8 weeks, during which 50 fish were randomly examined to check health condition through necropsy and microbiological tests to verify the absence of pathogens such as viruses, bacteria and parasites (Thoesen J. (1994) Suggested procedures for the detection and identification of finfish and shellfish Certain pathogens, 4th edn. Fish Health Section, American Fisheries Society, Bethesda, Md.; OIE (Office International des Epizooties) (2000) Diagnostic Manual for aquatic animal diseases, 3rd edn. OIE, Paris).

Fish were held in 1,000 L capacity fiberglass tanks each with independent water supply. The level of dissolved oxygen in the water was 10 mg/L. Water temperature, and oxygen levels of nitrogen compounds were controlled daily.

Extruded feed pellets (Micro 10, prepared by Ewos®) were used to prepare five diets with 0, 100, 200, 300 and 600 ppm of saponins/kg of feed (saponins from the commercial products Ultra Dry® 100-Q and Quillaja Dry® 100). These doses are equivalent to 0, 2, 4, 6 and 12 mg of saponins/kg of live weight of fish, respectively. The fish were divided into 10 individual tanks with 50 fish each (5 groups with duplicate).

Fishes were hand fed twice a day with diets according to the expected live weight and growth rate of fish. To do this the weight of fish where obtained at 0, 30 and 60 post-start of the experiment.

Fish were observed at least three times daily during the study, recording any possible clinical signs and mortalities. The experiment lasted 60 days. Results during the course of the trial showed no mortalities or abnormalities attributable to the product administered at the different doses. Additionally, no macro or microscopic pathological alterations in the liver or intestine in any treated group, compared to the control group, were found. In conclusion, Quillaja extracts were safe for administration at tested doses.

Example 2: Use of Quillaja Extracts for the Prevention and/or Treatment of In Vitro Viral Infections in Fish Antiviral Activity of Quillaja Extracts Against IPNv.

The antiviral activity of the extracts was measured through infection assay in CHSE-214 cell monolayers derived from salmon (Oncorhynchus tshawytscha, ATCC Number CRL-1681, American Type Culture Collection). This cell line was grown at 16° C. in culture medium (MEM, Gibco) supplemented with 10% Fetal Bovine Serum (Hyclone), 2 mM L-glutamine (Gibco), 10 mM HEPES (Hyclone), 100 IU mL$^{-1}$/100 µg/mL-1 of gentamicin (Gibco). The CHSE-214 cells were incubated in culture plates with 24 well plates at a confluence of 90%. To determine the antiviral activity, the culture medium was removed and the monolayer was infected with a viral suspension of a Chilean IPNv isolated with an approximate 50 plaque forming units (PFU) and different Quillaja extracts. After 1 hour of viral adsorption at 15° C., the inoculum was removed, and the cell monolayer was covered with agarose gel of low temperature of gelation at 0.5% in growth medium supplemented with different Quillaja extracts. It was incubated for 3 days at 15° C. and then the cells were fixed with 1 mL of 37% formaldehyde at room temperature for 1 hour. After removing the fixative and the agarose overlay, the cell monolayer was stained with 0.5% crystal violet solution for 1 hour. Finally, cells were washed with water and count of plaque forming units (PFU) was done. The efficiency of infection was quantified by the number of PFU obtained and compared with the percentage of the untreated control. Each condition was performed in triplicate.

Results showed that Quillaja extracts could effectively control the infection against the IPN virus, which is shown in Table 3. Of the extracts tested, Vax Sap®, Ultra Dry® 100-Q (UD 100 Q) and Quillaja Dry® 100 (QD 100) were highly effective at doses of 1.09; 1.46 and 0.73 µg/mL, respectively. Furthermore, it was observed that with a low concentration of saponins, 40% of uninfected monolayer (QL Perm® 1 and QL Perm® 2) was obtained.

TABLE 3

Efficacy (% uninfected cell layer) of Quillaja extracts concentrations according to products and saponin content in in vitro infections with IPNV.

| Product | Product concentration (µg/mL) | Saponin concentration (µg/mL) | Non-infected monolayer (%) |
|---|---|---|---|
| Positive Control | 0 | 0 | 0$^c$ |
| Vax Sap | 1.22 | 1.09 | 75 +/− 3.9$^a$ |
| UD 100 Q | 2.44 | 1.46 | 69.5 +/− 1.3$^{ab}$ |
| QD 100 | 2.44 | 0.73 | 59.1 +/− 1.2$^b$ |
| QL Perm 1 | 0.78 | 0.0078 | 43.9 +/− 2.2$^d$ |
| QL Perm 2 | 0.78 | 0.0078 | 45.8 +/− 1.4$^d$ |

Note:
$^{a,b,c}$ and $^d$ denote statistical differences at $p < 0.05$

Antiviral Activity of Quillaja Extracts Against ISAv.

Viral infection was carried out using approximately $1 \times 10^6$ cells of ASK cell line [Atlantic Salmon were sown. Kidney] (ATCC® CRL2747™), which grew into a 6-well plate to a confluence of 80 to 90%. The cells were cultivated at 16° C. in Leibovitz medium (L-15, Hyclone, Thermo Scientific), supplemented with gentamicin (50 µg/mL), L-glutamine (4 mM) (Gibco, Thermo Scientific), 2-mercaptoethanol 1% (v/v) (2-ME, Gibco), fetal bovine serum 10% (v/v) (FBS, Hyclone). To determine the antiviral efficacy, cells were incubated for 4 hours with the viral inoculum (Chilean isolate a viral titer of $10^6$ copies of viral RNA). Subsequently, the culture medium was removed and fresh culture medium supplemented with antibiotics and different Quillaja extracts was added. Infectivity was quantified by qRT-PCR technique. This technique allowed the quantification of the number of copies of viral RNA obtained as a result of a viral infection. Results were expressed as a percentage comparison between the number of copies produced in the untreated condition versus treated Quillaja extracts, according to Table 4. Each condition was performed in triplicate. All Quillaja extracts were able to control the in vitro infection above 95%.

TABLE 4

In vitro efficacy (viral proliferation decrease) of different concentrations of *Quillaja* extracts according to products and saponin content, against ISAv.

| Product | Product concentration (μg/mL) | Saponin concentration (μg/mL) | Viral copies/mL (10⁴) | Viral growth inhibition (%) |
|---|---|---|---|---|
| Positive control | 0 | 0 | 870,818 +/− 15,903 | 0$^a$ |
| VaxSap | 0.48 | 0.43 | 0.0005 +/− 0.0003 | >99$^b$ |
| UD 100 Q | 0.48 | 0.31 | 44,800 +/− 24,335 | 95$^b$ |
| QD 100 | 0.48 | 0.12 | 0.010 +/− 0.007 | >99$^b$ |
| QL 1000 | 7.8 | 0.78 | 0.006 +/− 0.003 | >99$^b$ |
| QL Perm 1 | 7.8 | 0.078 | 0.010 +/− 0.007 | >99$^b$ |
| QL Perm 2 | 7.8 | 0.078 | 0.046 +/− 0.003 | >99$^b$ |

Note:
$^{a,b,c}$ and $^d$ denote statistical differences at $p < 0.05$

Example 3: Preparation of a Fish Feed Impregnated with *Quillaja saponaria* Extracts

*Quillaja* extracts were mixed with fish oil to achieve the desired concentrations and then this mixture was impregnated at a rate of 4.9:1 (oil:dry pellet) in fish feed. This was done using an industrial mixer and incorporating oil in the food in movement for at least minutes additional mixing for at least 10 minutes.

To obtain a food composition impregnated with *Quillaja* extracts at the effective dose, important parameters to be considered are saponin doses/live weight of fish to be administered in the range from 0.9 to 12 mg of saponins per kilogram of live weight, fish weight and the amount of food they consume daily. The percentage of saponins in each particular *Quillaja* extract product should also be noted beforehand. Thus, any skilled person can obtain the ratio of saponins to be incorporated in the food.

As an example, to prepare a food composition considering the QL Perm® product, it must be used in a proportion of 6% w/w (60 g of product per kilogram of fish food).

Example 4: Use of *Quillaja* Extracts for the Prevention and/or Treatment of Viral Infections in In Vivo In Vivo Efficacy of *Quillaja* Products Against IPNv Two hundred and forty *Salmo salar* fry with an average weight of 5 to 6 g were used. Selected fishes had no history of ISAv, which was checked by sampling and subsequent analysis of molecular diagnosis by RT-PCR in real time. Additionally, fishes were checked for bacterial and viral diseases. Before transferring the fishes to the experimental station, 60 fish were randomly sampled to determine their health condition, which considered necropsy, gill inspection, intestine and skin sampling, Gram staining in internal organs (spleen, kidney and brain), staining with acridine orange in gills, IFAT analysis for BKD and SRS, and RT-PCR for IPNv. The general clinical appearance of the fish was acceptable and was within normal parameters for the salmon industry and therefore representative of the Chilean fish industry. This also includes the presence of some fish of the selected group as IPNv carriers.

During the test, fishes were fed with a diet of 15 micro EWOS 15CP® diet at a daily rate of 0.75% of body weight (bw/day) impregnated with a *Quillaja saponaria* extract in a dose of 3.75 mg product/Kg of body weight.

Experimental Infection with IPN Virus

Experimental infection with IPNv was performed by intraperitoneal injection in the ventral line at a rate of 0.1 mL of inoculum per fish, with a titer of 1×10⁸ viral copies genome/mL. Additionally, control groups were inoculated with culture medium without virus, in order that all fish were subject to the same management. To perform the inoculation, fish were anaesthetized with benzocaine in a separate reservoir tank at a dose of 40 to 60 ppm. Subsequently, fish recovered in fresh water tank without benzocaine and then were moved into their original experimental tanks, where they stayed during the trial.

Treatment with *Quillaja* Extracts

The administration was performed using *Quillaja* extracts given orally for 7 days before infection and then continued feeding with the extracts throughout the post-infection period. Each day, food was prepared using a dose of QD100 product as 3.75 mg of product/Kg body weight (bw) (500 mg product/Kg food), or a dose of UD100 of 3.75 mg product/Kg bw (500 mg product/Kg food), incorporated in 2% fish oil to the pellet. Table shows the test schedule indicated.

TABLE 5

Test schedule of the in vivo efficacy study using *Quillaja* extracts for the prevention and/or treatment against IPNv infections.

| Day | −10 | 0 | 1 | 7 | 45 |
|---|---|---|---|---|---|
| Acclimation | Start | End | | | |
| Oral treatment with extracts | | | Start | | End |
| IPN viral inoculation | | | | Start | |
| Post-infection follow up | | | | Start | End |
| Post-treatment follow up | | | | Start | End |
| Total time of study | | Start | | | End |

Subsequently, the efficacy of treatment with *Quillaja* extracts was evaluated and fish mortality was recorded daily. Table 6 shows the cumulative mortality data.

TABLE 6

Survival percentage of IPNv challenged fish fed with or without *Quillaja extracts*.

| Tanks | Total fish | Final fish | Mortality (%) | Survival (%) | Mean mortality | Mean survival |
|---|---|---|---|---|---|---|
| (1) Normal diet | 20 | 19 | 5 | 95 | 2.5 | 97.5 |
| (2) Normal diet | 20 | 20 | 0 | 100 | | |
| (7) Normal diet + IPNV | 20 | 10 | 50 | 50 | 47.5 | 52.5 |
| (8) Normal diet + IPNV | 20 | 11 | 45 | 55 | | |
| (3) UD100 diet | 20 | 19 | 5 | 95 | 5 | 95 |
| (4) UD100 diet | 20 | 19 | 5 | 95 | | |
| (9) UD100 + IPNV diet | 20 | 15 | 25 | 75 | 17.5 | 82.5 |
| (10) UD100 + IPNV diet | 20 | 18 | 10 | 90 | | |
| (5) QD100 diet | 20 | 20 | 0 | 100 | 5 | 95 |

TABLE 6-continued

Survival percentage of IPNv challenged fish fed with or without *Quillaja* extracts.

| Tanks | Total fish | Final fish | Mortality (%) | Survival (%) | Mean mortality | Mean survival |
|---|---|---|---|---|---|---|
| (6) QD100 diet | 20 | 18 | 10 | 90 | | |
| (11) QD100 + IPNV diet | 20 | 17 | 15 | 85 | 17.5 | 82.5 |
| (12) QD100 + IPNV diet | 20 | 16 | 20 | 80 | | |

Tanks 7, 8, 9, 10, 11 and 12 correspond to studies with fish inoculated with IPNv. The outbreak of mortality occurred between days 18 and 24 post-inoculation. The most mortality was observed in tanks that did not received oral administration of *Quillaja* extracts. Low mortality was observed in tanks who received oral administration of *Quillaja* extracts. Tanks with fish treated with *Quillaja* extracts practically did not develop the disease, compared to that observed in untreated tanks.

Later, all dead fish were necropsied. A non-specific clinical symptom in diseased fish was observed, such as lethargy, dark coloration and death. Microscopically, dead fish showed generally nonspecific signs such as pale necrotic liver and spleen.

The diagnosis was made in IPNv infected dead fish, with positive results for the detection of the virus by amplification by RT-PCR, which confirmed that the fish developed the infection and disease, although in some cases this was moderate.

Importantly, considering the high fish health risk involved in in vivo experimentation assays with ISA virus, and biosecurity protocols such as de duty to eliminate all fish in case of a virus outbreak, and considering the equivalent results obtained in in vitro and in vivo assays for IPNv, taking in consideration the in vitro results obtained for *Quillaja* extracts in inhibition of viral replication of ISAv from Table 3, which is greater than 99% in most cases, it is possible to infer that oral administration of these extracts, either as part of a food or a medicinal product, will also confer protection against ISAv to fish.

Thus, the results showed that the use of extracts of *Quillaja saponaria* for the prevention and/or control against viral diseases in fish is highly effective, which reflect a protective effect against ISA virus and IPN virus with over 90% of effectiveness. Also, it was demonstrated that in vivo efficacy was high for the prevention and/or control of viral infections at a concentration of 0.9375 mg/Kg of total saponins per live weight of fish using *Quillaja* natural extracts on a controlled infection of Atlantic salmon, achieving a decrease in mortality associated with IPNv of at least 72%.

The invention claimed is:

1. A method for controlling a viral disease caused by the Infectious Pancreatic Necrosis virus (IPNv) in *Salmo salar* fish, wherein said method comprises administering to *Salmo salar* fish an effective amount of a medicinal composition comprising a *Quillaja saponaria* extract as active ingredient and an appropriate excipient; wherein said *Quillaja saponaria* extract contains saponins.

2. The method according to claim 1, wherein the medicinal composition is administered to the fish orally in a dose ranging from 0.9 to 12 mg saponins/kg of live weight of fish per day.

3. The method according to claim 2, wherein the medicinal composition is administered to the fish in combination with fish food.

* * * * *